United States Patent [19]

Guthikonda et al.

[11] Patent Number: 5,409,920
[45] Date of Patent: Apr. 25, 1995

[54] 2-(3-PYRIDYL)-CARBAPENEM ANTIBACTERIAL AGENTS

[75] Inventors: Ravindra N. Guthikonda, Edison; Frank P. DiNinno, Old Bridge, both of N.J.

[73] Assignee: Merck & Co., Inc., Rahway, N.J.

[21] Appl. No.: 593,849

[22] Filed: Oct. 5, 1990

[51] Int. Cl.⁶ .................. A01N 43/00; A61K 31/395; C07D 487/00
[52] U.S. Cl. ..................................... 514/210; 540/302
[58] Field of Search ......................... 540/302; 514/210

[56] References Cited

U.S. PATENT DOCUMENTS

| | | | |
|---|---|---|---|
| 4,260,627 | 4/1981 | Christensen et al. | 424/274 |
| 4,465,632 | 8/1984 | Christensen et al. | 260/245.2 |
| 4,543,257 | 9/1985 | Cama et al. | 514/210 |
| 4,775,669 | 10/1988 | Cama et al. | 514/210 |
| 4,962,101 | 10/1990 | DiNinno et al. | |

FOREIGN PATENT DOCUMENTS 0277743  8/1988  European Pat. Off. .

OTHER PUBLICATIONS

L. D. Cama et al., Total Synthesis of Thienamycin Analogs-III, Tetrahedron 39, 2531 (1983).
R. N. Guthikonda, et al., Structure Activity Relationships in the 2-Arylcarbapenem Series, *J. Med. Chem.*, 30, 871 (1987).

*Primary Examiner*—Johann Richter
*Assistant Examiner*—Rebecca Cook
*Attorney, Agent, or Firm*—Richard C. Billups; Mark R. Daniel; Joseph F. DiPrima

[57] ABSTRACT

Carbapenems of the formula

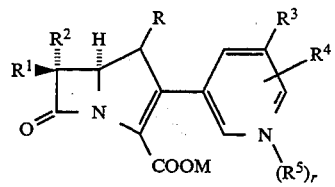

are useful antibacterial agents.

12 Claims, No Drawings

2-(3-PYRIDYL)-CARBAPENEM ANTIBACTERIAL AGENTS

BACKGROUND OF THE INVENTION

The present invention relates to antibacterial agents of the carbapenem class, in which the 2-position sidechain is characterized by a 3-pyridine moiety, substituted by various substituents, as described in more detail further below.

Thienamycin was an early carbapenem antibacterial agent having a broad spectrum; it has the following formula:

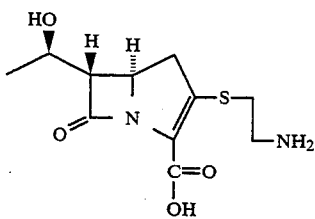

Later, N-formimidoyl thienamycin was discovered; it has the formula:

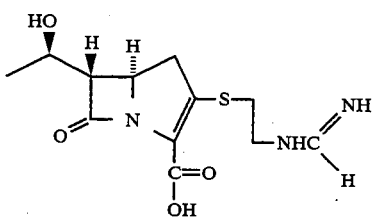

The 2-(3-pyridyl)carbapenems of the present invention are not characterized by a broad antibacterial spectrum such as that of thienamycin or N-formimidoyl thienamycin. Rather their spectrum of activity is largely limited to gram positive microorganisms, especially methicillin resistant *Stphylococcus aureus* (MRSA), methicillin resistant *Staphylococcus epidermidis* (MRSE), and methicillin resistant coagulase negative Staphylococci (MRCNS), and some gram negative organisms. The antibacterial compounds of the present invention thus comprise an important contribution to therapy of these difficult to control pathogens. Moreover, there is an increasing need for agents effective against such pathogens (MRSA/MRCNS) which are at the same time safe, i.e., free from undesirable toxic side effects. No β-lactam antibacterial has yet been found which meets these requirements. And, the current agent of choice, vancomycin, a glycopeptide antibacterial, is experiencing an ever increasing amount of resistance in the MRSA/MRCNS pathogens.

More recently, carbapenem antibacterial agents have been described which have a 2-substituent which is an aryl moiety optionally substituted by, e.g., aminomethyl and substituted aminomethyl. These agents are described in U.S. Pat. Nos. 4,543,257 and 4,260,627 and have the formula:

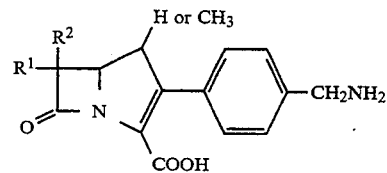

A related patent, U.S. Pat. No. 4,775,669, by L. Cama and B. G. Christensen describes the unsubstituted 2-(4- and 2-pyridyl)-carbapenems:

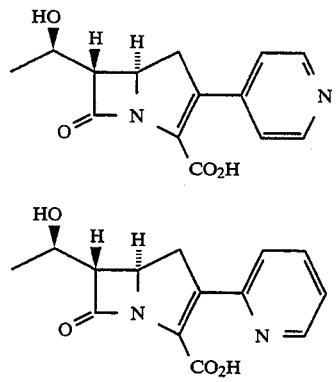

as having broad spectrum antibacterial activity. The patent generically claims substituted 2-heteroaryl-carbapenems, which includes a substituted pyridine. The compounds of the present invention, substituted 2-(3-pyridyl)carbapenems are not specifically disclosed in this reference nor does the patent report these 2-heteroaryl-carbapenem compounds as having anti-methicillin resistant *Staphylococcus aureus* (MRSA) activity. The 2-(5-substituted-3-pyridyl)carbapenems of the present invention with a select group of substituents at 5-position of pyridine nucleus have been found to impart surprisingly high anti-MRSA activity.

EP-A-0277 743 describes a particular class of compounds of the formula:

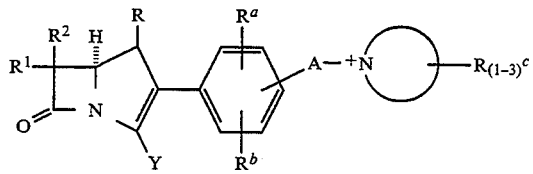

but this limited teaching in no way suggests the totally different compounds of the present invention, nor their surprisingly better anti-MRSA/MRCNS activity.

SUMMARY OF THE INVENTION

The present invention provides novel carbapenem compounds of the formula:

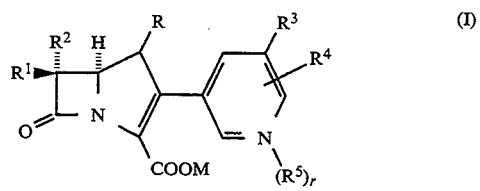

wherein:

R is H or $CH_3$;

$R^1$ and $R^2$ are independently H, $CH_3-$, $CH_3CH_2-$, $(CH_3)_2CH-$, $HOCH_2-$, $CH_3CH(OH)-$, $(CH_3)_2C(OH)-$, $FCH_2CH(OH)-$, $F_2CHCH(OH)-$, $F_3CCH(OH)-$, $CH_3CH(F)-$, $CH_3CF_2-$, or $(CH_3)_2C(F)-$;

$R^3$ is
- a) a halogen atom —Br, —Cl, —F, selected from the group consisting of —I;
- b) a sulfur radical which is $-S(O)_nR^s$, where n=0-2, and $R^s$ as defined below;
- c) aryl, where aryl is phenyl or napthyl optionally mono-substituted with $R^4$ as defined below;
- d) heteroaryl, where heteroaryl is a monocyclic aromatic hydrocarbon group having 5 or 6 ring atoms, in which a carbon atom is the point of attachment, in which one of the carbon atoms has been replaced by a nitrogen atom, in which one additional carbon atom is optionally replaced by a heteroatom selected from O or S, in the case of a 5-membered heterocyle, and in which from 1 to 3 additional carbon atoms are optionally replaced by a nitrogen heteroatom, and where the heteroaryl is optionally mono-substituted with $R^4$, as defined below; or
- e) heteroaryl, as defined above, substituted on the nitrogen with $R^5$ defined below; and $R^4$ is hydrogen or is selected from the group consisting of:
- a) a trifluoromethyl group which is $-CF_3$;
- b) $C_1-C_4$ alkoxy radical which is $-OC_{1-4}$ alkyl, wherein the alkyl is optionally mono-substituted by $R^q$, where
  - $R^q$ is a member selected from the group consisting of —OH, $-OCH_3$, —CN, $-C(O)NH_2$, $-OC(O)NH_2$, CHO, $-OC(O)N(CH_3)_2$, $-SO_2NH_2$, $-SO_2N(CH_3)_2$, $-SOCH_3$, $-SO_2CH_3$, —F, $-CF_3$, $-COOM^a$ (where $M^a$ is hydrogen, alkali metal, methyl or phenyl), tetrazolyl (where the point of attachment is the carbon atom of the tetrazole ring and one of the nitrogen atoms is mono-substituted by $M^a$ as defined above) and $-SO_3M^b$ (where $M^b$ is hydrogen or an alkali metal);
- c) a hydroxy group which is —OH;
- d) a carbonyloxy radical which is $-O(C=O)R^s$, where
  - $R^s$ is $C_{1-4}$ alkyl or phenyl, each of which is optionally mono-substituted by $R^q$ as defined above;
- e) a carbamoyloxy radical which is $O(C=O)N(R^y)R^z$, where
  - $R^y$ and $R^z$ are independently H, $C_{1-4}$ alkyl (optionally mono-substituted by $R^q$ as defined above), together a 3- to 5-membered alkylidene radical to form a ring (optionally substituted with $R^q$ as defined above) or together a 2- to 4-membered alkylidene radical, interrupted by —O—, —S—, —S(O)— or $-S(O)_2-$ to form a ring (where the ring is optionally mono-substituted with $R^q$ as defined above);
- f) a sulfur radical which is $-S(O)_n-R^s$ where n=0-2, and $R^s$ is defined above;
- g) a sulfamoyl group: $-SO_2N(R^y)R^z$ where $R^y$ and $R^z$ are as defined above;
- h) azido: $N_3$;
- i) a formamido group: $-N(R^t)(C=O)H$, where $R^t$ is H or $C_{1-4}$ alkyl, and the alkyl thereof is optionally monosubstituted by $R^q$ as defined above;
- j) a $(C_1-C_4$ alkyl)carbonylamino radical which is $-N(R^t)(C=O)C_{1-4}$ alkyl, where $R^t$ is as defined above, and the alkyl group is also optionally mono-substituted by $R^q$ as defined above;
- k) a $(C_1-C_4$ alkoxy)carbonylamino radical which $-N(R^t)(C=O)OC_{1-4}$ alkyl, where $R^t$ is as defined above, and the alkyl group is also optionally mono-substituted by $R^q$ as defined above;
- l) a ureido group which is $-N(R^t)(C=O)N(R^y)R^z$ where $R^t$, $R^y$ and $R^z$ are as defined above;
- m) a sulfonamido group which is $-N(R^t)SO_2R^s$, where $R^s$ and $R^t$ are as defined above;
- n) a cyano group which is —CN;
- o) a formyl or acetalized formyl radical selected from the group consisting of $-(C=O)H$ and $-CH(OCH_3)_2$;
- p) $(C_1-C_4$ alkyl)carbonyl radical wherein the carbonyl is acetalized: $-C(OCH_3)_2C_{1-4}$ alkyl, where the alkyl is optionally mono-substituted by $R^q$ as defined above;
- q) carbonyl radical which is $-(C=O)R^s$, where $R^s$ is as defined above;
- r) $-(C=NOR^z)R^y$ where $R^y$ and $R^z$ are as defined above, except they may not be joined together to form a ring;
- s) a $(C_1-C_4$ alkoxy)carbonyl radical which is $-(C=O)OC_{1-4}$ alkyl, where the alkyl is optionally mono-substituted by $R^q$ as defined above;
- t) a carbamoyl radical which is $-(C=O)N(R^y)R^z$ where $R^y$ and $R^z$ are as defined above;
- u) an N-hydroxycarbamoyl or $N(C_1-C_4$ alkoxy) carbamoyl radical in which the nitrogen atom may be additionally substituted by a $C_1-C_4$ alkyl group which is $-(C=O)-N(OR^y)R^z$ where $R^y$ and $R^z$ are as defined above, except they may not be joined together to form a ring;
- v) a thiocarbamoyl group which is $-(C=S)N(R^y)R^z$ where $R^y$ and $R^z$ are as defined above;
- w) carboxyl: $-COOM^b$, where $M^b$ is as defined above;
- x) thiocyanate which is —SCN;
- y) trifluoromethylthio which is $-SCF_3$;
- z) an amino group, $N(R^t)_2$, wherein $R^t$ is as defined above;
- aa) an anionic function selected from the group consisting of:
  - phosphono which is $[P=O(OM^b)_2]$; alkylphosphono which is $\{P=O(OM^b)-[O(C_1-C_4$ alkyl$)]\}$; alkylphosphinyl which is $[P=O(OM^b)-(C_1-C_4\text{-alkyl})]$; phosphoramido which is $[P=O(OM^b)N(R^y)R^z$ and $P=O(OM^b)NHR^x]$; sulfino which is $(SO_2M^b)$; sulfo which is $(SO_3M^b)$; acylsulfonamides selected from the structures: $CONM^bSO_2R^x$, $CONM^bSO_2N(R^y)R^z$, $SO_2NM^bCON(R^y)R^z$; and $SO_2NM^bCN$, where
    - $R^x$ is phenyl or heteroaryl, where heteroaryl is a monocyclic aromatic hydrocarbon group having 5 or 6 ring atoms, in which a carbon atom is the point of attachment, in which one of the carbon atoms has been replaced by a nitrogen atom, in which one additional carbon atom is optionally replaced by a heteroatom selected from O or S, and in which from 1 to 2 additional carbon atoms are optionally replaced by a nitrogen heteroatom, and where the phenyl and heteroaryl are optionally monosubstituted by $R^q$, as defined above; $M^b$ is as defined above; and $R^y$ and $R^z$ are as defined above;

ab) $C_5$–$C_7$ cycloalkyl group in which one of the carbon atoms in the ring is replaced by a heteroatom selected from O, S, NH, or N($C_1$–$C_4$ alkyl) and in which one additional carbon may be replaced by NH or N($C_1$–$C_4$ alkyl), and in which at least one carbon atom adjacent to each nitrogen heteroatom has both of its attached hydrogen atoms replaced by one oxygen thus forming a carbonyl moiety and there are one or two carbonyl moieties present in the ring;

ac) $C_2$–$C_4$ alkenyl radical, optionally monosubstituted by one of the substituents a) to ac) above and phenyl which is optionally substituted by $R^q$ as defined above;

ad) $C_2$–$C_4$ alkynyl radical, optionally monosubstituted by one of the substituents a) to ac) above;

ae) $C_1$–$C_4$ alkyl radical;

af) $C_1$–$C_4$ alkyl mono-substituted by one of the substituents a)–ac) above;

ag) a 2-oxazolidinonyl moiety in which the point of attachment is the nitrogen atom of the oxazolidinone ring, the ring oxygen atom is optionally replaced by a heteroatom selected from S and $NR^t$ (where $R^t$ is as defined above) and one of the saturated carbon atoms of the oxazolidinone ring is optionally mono-substituted by one of the substituents a) to ag) above;

ah) aryl, where aryl is phenyl or napthyl optionally mono-substituted with $R^q$ as defined above;

ai) heteroaryl, where heteroaryl is a monocyclic aromatic hydrocarbon group having 5 ring atoms, in which a carbon atom is the point of attachment, in which one of the carbon atoms has been replaced by a heteroatom selected from O or S, such as furan or thiophene; and $R^5$ is amino ($NH_2$), oxygen or ($C_1$–$C_4$)alkyl, to give a quaternary nitrogen group such as an N-amino or an N-oxide or ($C_1$–$C_4$)alkyl hetercarylium; and r is 0 and 1; and M is selected from:
i) hydrogen;
ii) a pharmaceutically acceptable esterifying group or removable carboxyl protecting group;
iii) an alkali metal or other pharmaceutically acceptable cation; or
iv) a negative charge which is balanced by a cationic group.

DETAILED DESCRIPTION OF THE INVENTION

The compounds of Formula I may be prepared in a three stage synthesis scheme followed by removal of protecting groups. The objective of the first synthesis stage is to prepare the substituted pyridine substituent. Schemes 1 and 2 demonstrate synthetic routes to several of the $R^a$ substituents starting with commercially available 3,5-dibromopyridine (Aldrich, D4,310-7). The objective of the second synthesis stage is to attach the pyridine substituent to the carbapenem as shown in Scheme 3 with the preparation of the pyridyl Grignard reagent and coupling of the Grignard to the azetidinone 4a to glove the pyridyl adduct 4b. Cyclization of 4b is accomplished by heating in xylene to give the protected carbapenem 4c which can be deprotected as described. A final synthesis stage involves the quaternarization of the pyridyl substitutent described in Scheme 5 utilizing the protected carbapenem 4c.

SCHEME 1

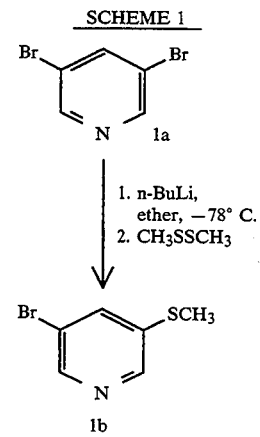

In Scheme 1, treatment of commercially available 3,5-dibromopyridine 1a with alkyllithiums, such as n-butyllithium in a solvent such as ether at a temperature around −78° C. gives a lithium salt, as the result of metal-halogen exchange, which can be treated with disulfides such as dimethyldisulfide or the like, to give the bromomethylthiopyridine 1b.

SCHEME 2

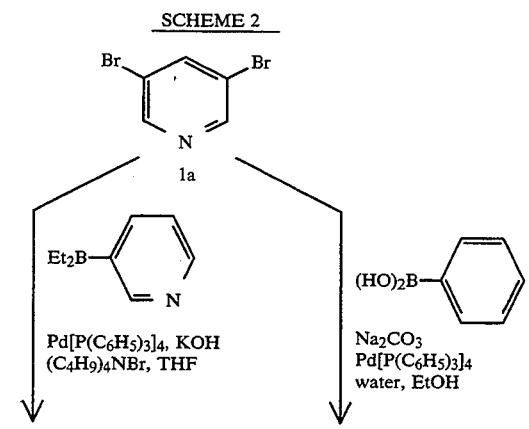

SCHEME 2

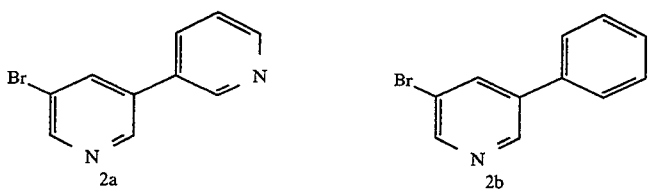

SCHEME 3

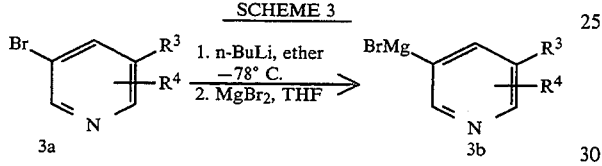

In Scheme 2, palladium catalyzed coupling of 3-pyridyldiethylborane and phenylboronic acid with 3,5-dibromopyridine 1a in presence of base gives the coupling products 2a and 2b respectively. In Scheme 3, the preparation of the Grignard reagents 3b can be achieved by treating a bromopyridine 3a, such as 2a or 2b, with an alkyllithium reagent, such as n-butyllithium in ether and then reacting with a freshly prepared solution of magnesium bromide in tetrahydrofuran. The resulting solution of the Grignard reagent is then added to a solution of the pyridyl thioester synthon, as shown in Scheme 4, in a solvent such as tetrahydrofuran at a temperature of from −20° C. to 0° C., to give the ketone, 4b. The ylide ketone 4b on heating in xylene at a temperature of from 90° to 140° C. for from 1 to 4 hours cyclizes to generate the protected carbapenem 4c. The deprotection of the carbapenem is carried out by palladium catalyzed deallylation in a solution containing sodium 2-ethylhexanoate to give the desired carbapenem 4d.

SCHEME 4

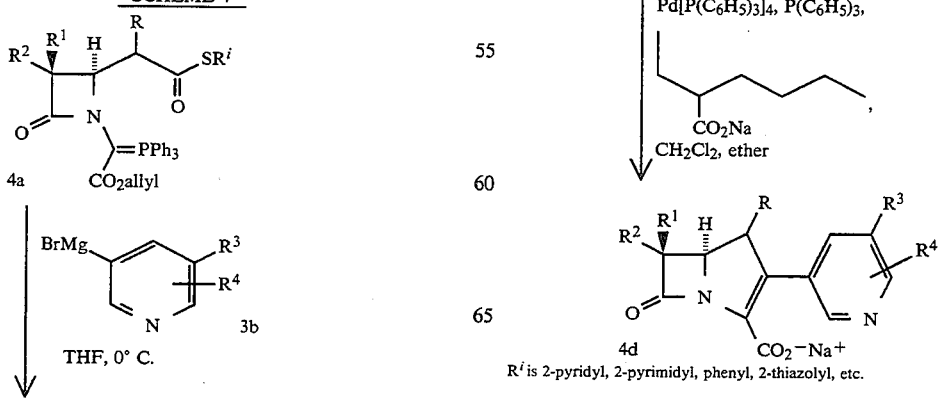

$R^i$ is 2-pyridyl, 2-pyrimidyl, phenyl, 2-thiazolyl, etc.

SCHEME 5

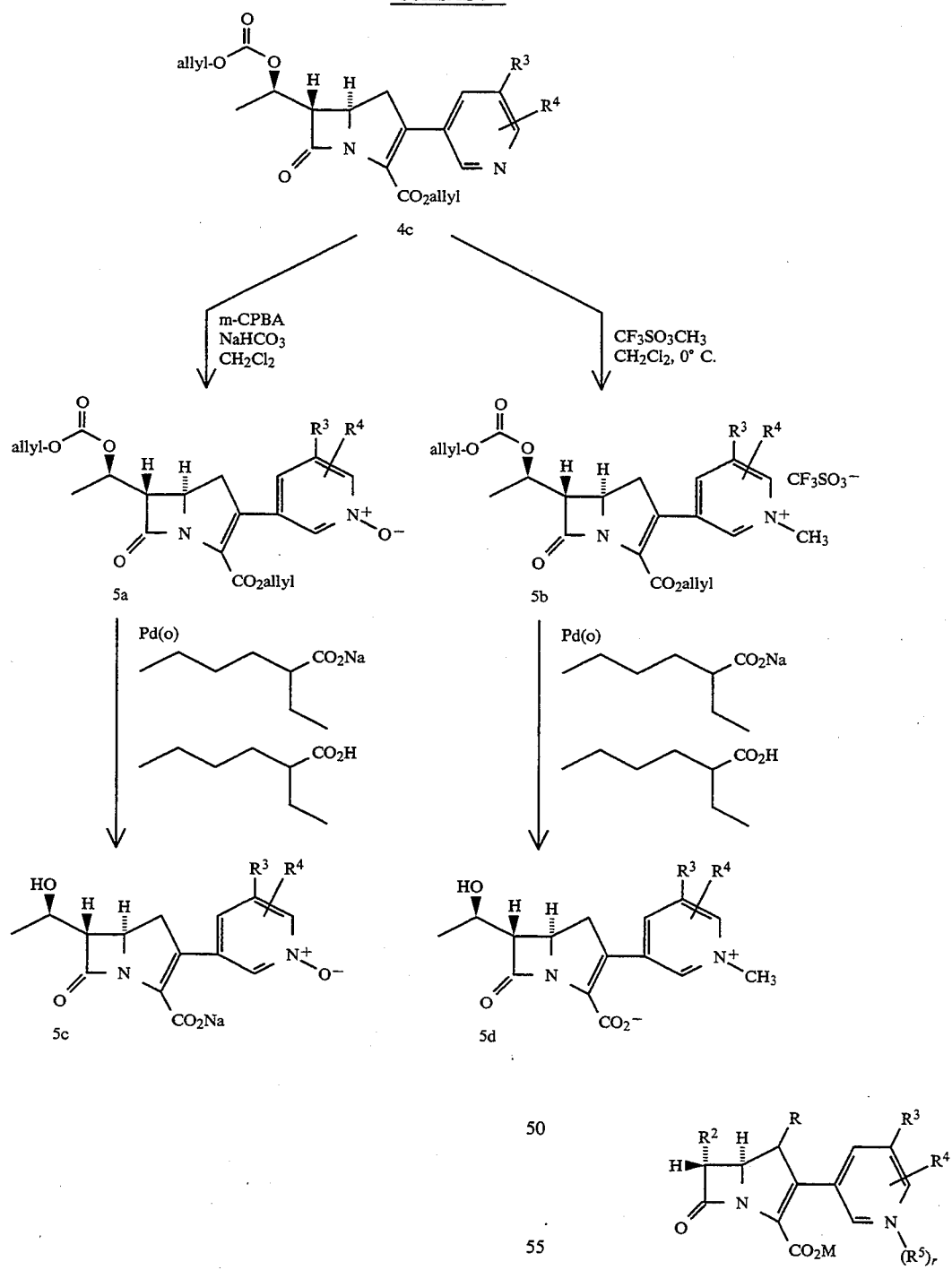

The protected 2-pyridylcarbapenem, 4c can be oxidized to the N-oxide 5a by treating with m-chloroperoxybenzoic acid in dichloromethane. Deprotection of the N-oxide in the manner described in Scheme 5 will produce the sodium salt 5c. The carbapenem 4c can also be quarternized with methyl trifluoromethanesulfonate in dichloromethane at 0° C. to give the N-methyl analog 5b. Again, palladium catalyzed deallylation of 5b affords the zwitterionic carbapenem 5d.

The compounds of the structural formula below are representative of the instant invention:

and the substituents are as defined in the Table I below and when $R^5$ is present the pyridyl nitrogen carries a positive charge which in turn is counterbalanced by M being a negative charge. It is understood that the stereochemistry of $R^2$ substituents which contain a chiral center (1-fluoroethyl or 1-hydroxyethyl) is the (R)-configuration in all of the listed compounds:

TABLE I

| Ex. | R | $R^2$ | M | $R^3$ | $R^4$ | $R^5$ |
|---|---|---|---|---|---|---|
| 1 | H | CH(OH)CH$_3$ | Na$^+$ | Br | H | — |
| 2 | H | CH(OH)CH$_3$ | Na$^+$ | phenyl | H | — |

TABLE I-continued

| Ex. | R | $R^2$ | M | $R^3$ | $R^4$ | $R^5$ |
|---|---|---|---|---|---|---|
| 3 | H | CH(OH)CH$_3$ | Na$^+$ | 3-pyridyl | H | — |
| 4 | H | CH(OH)CH$_3$ | Na$^+$ | SCH$_3$ | H | — |
| 5 | H | CH(OH)CH$_3$ | Na$^+$ | SO$_2$CH$_3$ | H | — |
| 6 | H | CH(OH)CH$_3$ | Na$^+$ | SOCH$_3$ | H | — |
| 7 | H | CH(OH)CH$_3$ | (—) | SCH$_3$ | H | CH$_3$ |
| 8 | H | CH(OH)CH$_3$ | (—) | Br | H | CH$_3$ |
| 9 | H | CH(OH)CH$_3$ | (—) | phenyl | H | CH$_3$ |
| 10 | H | CH(OH)CH$_3$ | (—) | SOCH$_3$ | H | CH$_3$ |
| 11 | H | CH(OH)CH$_3$ | (—) | SO$_2$CH$_3$ | H | CH$_3$ |
| 12 | H | CH(F)CH$_3$ | Na$^+$ | Br | H | — |
| 13 | H | CH(F)CH$_3$ | (—) | Br | H | CH$_3$ |
| 14 | H | CH(F)CH$_3$ | Na$^+$ | phenyl | H | — |
| 15 | H | CH(F)CH$_3$ | (—) | phenyl | H | CH$_3$ |
| 16 | H | CH(F)CH$_3$ | Na$^+$ | 3-pyridyl | H | — |
| 17 | H | CH(F)CH$_3$ | Na$^+$ | SCH$_3$ | H | — |
| 18 | H | CH(F)CH$_3$ | Na$^+$ | SOCH$_3$ | H | — |
| 19 | H | CH(F)CH$_3$ | Na$^+$ | SO$_2$CH$_3$ | H | — |
| 20 | H | CH(F)CH$_3$ | (—) | SCH$_3$ | H | CH$_3$ |
| 21 | H | CH(F)CH$_3$ | (—) | SOCH$_3$ | H | CH$_3$ |
| 22 | H | CH(F)CH$_3$ | (—) | SO$_2$CH$_3$ | H | CH$_3$ |
| 23 | CH$_3$ | CH(OH)CH$_3$ | Na$^+$ | Br | H | — |
| 24 | CH$_3$ | CH(OH)CH$_3$ | Na$^+$ | SCH$_3$ | H | — |
| 25 | CH$_3$ | CH(F)CH$_3$ | Na$^+$ | Br | H | — |
| 26 | CH$_3$ | CH(F)CH$_3$ | Na$^+$ | SCH$_3$ | H | — |
| 27 | H | CH(OH)CH$_3$ | H | Br | NH$_2$ | — |
| 28 | H | CH(OH)CH$_3$ | (—) | Br | NH$_2$ | CH$_3$ |
| 29 | H | CH(OH)CH$_3$ | Na$^+$ | Br | CHO | — |
| 30 | H | CH(OH)CH$_3$ | Na$^+$ | SCH$_3$ | CHO | — |
| 31 | H | CH(OH)CH$_3$ | H | SCH$_3$ | NH$_2$ | — |
| 32 | H | CH(OH)CH$_3$ | (—) | SCH$_3$ | NH$_2$ | CH$_3$ |

The carbapenem compounds of the present invention are useful per se and in their pharmaceutically acceptable salt and ester forms in the treatment of bacterial infections in animal and human subjects. The term "pharmaceutically acceptable ester or salt" refers to those salt and ester forms of the compounds of the present invention which would be apparent to the pharmaceutical chemist. i.e., those which are non-toxic and which would favorably affect the pharmacokinetic properties of said compounds, their palatability, absorption, distribution, metabolism and excretion. Other factors, more practical in nature, which are also important in the selection, are cost of the raw materials, ease of crystallization, yield, stability, hygroscopicity, and flowability of the resulting bulk drug. Conveniently, pharmaceutical compositions may be prepared from the active ingredients in combination with pharmaceutically acceptable carriers. Thus, the present invention is also concerned with pharmaceutical compositions and methods of treating bacterial infections utilizing as an active ingredient the novel carbapenem compounds of the present invention.

The pharmaceutically acceptable salts referred to above may take the form —COOM. The M may be an alkali metal cation such as sodium or potassium. Other pharmaceutically acceptable cations for M may be calcium, magnesium, zinc, ammonium, or alkylammonium cations such as tetramethylammonium, tetrabutylammonium, choline, triethylhydroammonium, meglumine, triethanolhydroammonium, etc.

The pharmaceutically acceptable salts referred to above may also include non-toxic acid addition salts. Thus, the Formula I compounds can be used in the form of salts derived from inorganic or organic acids. Included among such salts are the following: acetate, adipate, alginate, aspartate, benzoate, benzenesulfonate, bisulfate, butyrate, titrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalare, pamoate, pectinate, persulfate, 3-phenylpropionate, pictate, pivalate, propionate, succinate, tartrate, thiocyanate, tosylate, and undecanoate.

The pharmaceutical acceptable esters of the novel carbapenem compounds of the present invention are such as would be readily apparent to a medicinal chemist, and include, for example, those described in detail in U.S. Pat. No. 4,309,438, Column 9, line 61 to Column 12, line 51. Included within such pharmaceutically acceptable esters are those which are hydrolyzed under physiological conditions, such as pivaloyloxymethyl, acetoxymethyl, phthalidyl, indanyl and methoxymethyl, and those described in detail in U.S. Pat. No. 4,479,947.

The novel carbapenem compounds of the present invention may take the form COOM, where M is a readily removable carboxyl protecting group. Such conventional blocking groups consist of known ester groups which are used to protectively block the carboxyl group during the synthesis procedures described above. These conventional blocking groups are readily removable, i.e., they can be removed, if desired, by procedures which will not cause cleavage or other disruption of the remaining portions of the molecule. Such procedures include chemical and enzymatic hydrolysis, treatment with chemical reducing or oxidizing agents under mild conditions, treatment with a transition metal catalyst and a nucleophile, and catalytic hydrogenation. Examples of such ester protecting groups include benzhydryl, p-nitrobenzyl, 2-naphthylmethyl, allyl, benzyl, trichloroethyl, silyl such as trimethylsilyl or t-butyldimethylsilyl, trimethylsilylethyl, phenacyl, p-methoxybenzyl, acetonyl, o-nitrobenzyl, p-methoxyphenyl, 4-pyridylmethyl, and t-butyl.

The compounds of the present invention are valuable antibacterial agents active against various Gram-positive and Gram-negative bacteria and accordingly find utility in human and veterinary medicine. The antibacterials of the invention are not limited to utility as medicaments; they may be used in all manner of industry, for example: additives to animal feed, preservation of food, disinfectants, and in other industrial systems where control of bacterial growth is desired. For example, they may be employed in aqueous compositions in concentrations ranging from 0.1 to 100 parts of antibiotic per million parts of solution in order to destroy or inhibit the growth of harmful bacteria on medical and dental equipment and as bactericides in industrial applications, for example in waterbased paints and in the white water of paper mills to inhibit the growth of harmful bacteria.

The compounds of this invention may be used in any of a variety of pharmaceutical preparations. They may be employed in capsule, powder form, in liquid solution, or in suspension. They may be administered by a variety of means; those of principal interest include: topically or parenterally by injection (intravenously or intramuscularly).

Compositions for injection, a preferred route of delivery, may be prepared in unit dosage form in ampules, or in multidose containers. The compositions may take such forms as suspensions, solutions, or emulsions in oily or aqueous vehicles, and may contain formulatory agents. Alternatively, the active ingredient may be in powder from for reconstitution, at the time of delivery, with a suitable vehicle, such as sterile water. Topical applications may be formulated in hydrophobic or hydrophilic bases as ointments, creams, lotions, paints, or powders.

The dosage to be administered depends to a large extent upon the condition and size of the subject being treated as well as the route and frequency of administration, the parenteral route by injection being preferred for generalized infections. Such matters, however, are left to the routine discretion of the therapist according to principles of treatment well known in the antibacterial art. Another factor influencing the precise dosage regimen, apart from the nature of the infection and peculiar identity of the individual being treated, is the molecular weight of the chosen species of this invention.

The compositions for human delivery per unit dosage, whether liquid or solid, may contain from 0.1% to 99% of active material, the preferred range being from about 10–60%. The composition will generally contain from about 15 mg to about 1500 mg of the active ingredient; however, in general, it is preferable to employ a dosage amount in the range of from about 250 mg to 1000 mg. In parenteral administration, the unit dosage is usually the pure compound I in sterile water solution or in the form of a soluble powder intended for solution.

The preferred method of administration of the Formula I antibacterial compounds is parenteral by i.v. infusion, i.v. bolus, or i.m. injection.

For adults, 5–50 mg of Formula I antibacterial compounds per kg of body weight given 2, 3, or 4 times per day is preferred. Preferred dosage is 250 mg to 1000 mg of the Formula I antibacterial given two (b.i.d.) three (t.i.d.) or four (q.i.d.) times per day. More specifically, for mild infections a dose of 250 mg t.i.d. or q.i.d. is recommended. For moderate infections against highly susceptible gram positive organisms a dose of 500 mg t.i.d. or q.i.d. is recommended. For severe, life-threatening infections against organisms at the upper limits of sensitivity to the antibiotic, a dose of 1000 mg t.i.d. or q.i.d. is recommended.

For children, a dose of 5–25 mg/kg of body weight given 2, 3, or 4 times per day is preferred; a dose of 10 mg/kg t.i.d. or q.i.d. is usually recommended.

Antibacterial compounds of Formula I are of the broad class known as carbapenems or 1-carbadethiapenems. Naturally occuring carbapenems are susceptible to attack by a renal enzyme known as dehydropeptidase (DHP). This attack or degradation may reduce the efficacy of the carbapenem antibacterial agent. The compounds of the present invention, on the other hand, are significantly less subject to such attack, and therefore may not require the use of a DHP inhibitor. However, such use is optional and contemplated to be part of the present invention. Inhibitors of DHP and their use with carbapenem antibacterial agents are disclosed in the prior art [see European Patent Applications No. 79102616.4, filed Jul. 24, 1979 (Patent No. 0 007 614); and NO. 82107174.3, filed Aug. 9, 1982 (Publication No. 0 072 014)].

The compounds of the present invention may, where DHP inhibition is desired or necessary, be combined or used with the appropriate DHP inhibitor as described in the aforesaid patents and published application. The cited European Patent Applications define the procedure for determining DHP susceptibility of the present carbapenems and disclose suitable inhibitors, combination compositions and methods of treatment. A preferred weight ratio of Formula I compound: DHP inhibitor in the combination compositions is about 1:1. A preferred DHP inhibitor is 7-(L-2-amino-2-carboxyethylthio) -2-<2,2-dimethylcyclopropanecarboxamide) -2-heptenoic acid or a useful salt thereof.

The invention is further defined by reference to the following examples, which are illustrative and not limiting. All temperatures are in degrees Celsius. All NMR spectra are measured in CDCl$_3$ solvent unless otherwise specified.

EXAMPLE 1

Sodium (5R,6S)-2-[3-(5-bromopyridyl)-6-[(1R)-hydroxyethyl]-carbapen-2-em-3-carboxylate

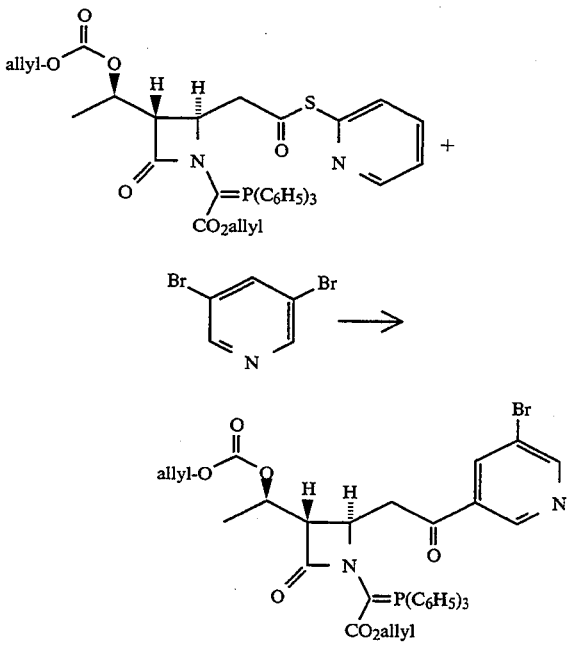

Step A: Preparation of (3S,4R)-1-[[(Allyloxy)carbonyl)](triphenylphosphoranylidene)methyl]-3-[(1R)-1-[allyloxycarbonyloxy)ethyl]-4-[(1R)-2'-[[3-(5-bromo)-pyridyl)]carbonyl]-ethyl]azetidin-2-one Finely powdered 3,5-dibromopyridine (711 mg; 3 mM) was added to 12 mL of ether at −78° C. under nitrogen. After stirring 5 minutes, n-butyllithium (2.5M solution; 1.32 mL, 3.3 mM) was added dropwise and stirring was continued for 30 minutes at −78° C. A freshly prepared magnesium bromide solution [from 168 mg of magnesium (7 mM) and 523 µl (6 mM) of ethylene bromide in 24 mL of tetrahydrofuran] was slowly added at −78° C. The reaction mixture was stirred at −78° C. for 15 minutes and then at 0° C. for 30 minutes, and the resulting turbid solution was used as the required Grignard reagent.

This Grignard solution was added dropwise to a solution of 1.0 g (~1.4 mM) of (3S,4R)-1-[[(allyloxy)-carbonyl](triphenylphosphoranylidene)methyl]-3-[(1R)-1-[(allyloxycarbonyloxy)ethyl]-4-[(1R) -2'-[(pyridylthio)carbonyl]ethyl]azetidin-2-one in 5 mL of tetrahydrofuran at 0° C. under nitrogen. After stirring 20 minutes at 0° C., 10 mL of saturated ammonium chloride solution was added, diluted with 20 mL of ethyl acetate and washed with 3×10 ml of saturated sodium chloride solution after drying over anhydrous magnesium sulfate, solvent was removed from the organic phase to give a crude oil, which was chromatographed on silica gel using ethyl acetate: hexane (7:3) mixture to give 269 mg of the desired ylide ketone as a yellow foam.

IR (cm$^{-1}$): 1740 (β-lactam C=O); 1690 (aromatic C=O); 1620–1645 (ylide C=O)

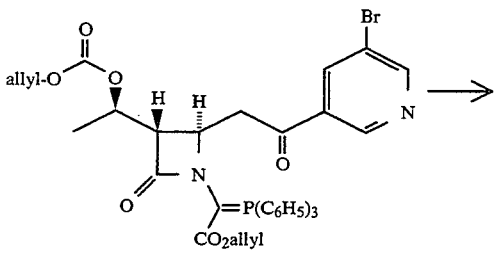

Step B: Preparation of Allyl (5R,6S)-2-[3-(5-bromo-pyridyl)]-6-[(1R)-allyloxycarbonyloxyethyl]-carbapen-2-em-3-carboxlate A solution of the ylide ketone 3 (R$^3$=Br), (230 mg) in 2 mL of xylene was heated 1.5 hours at 130° C. After cooling to R.T., the reaction mixture was applied on silica gel (10 g) packed wet with hexane. Elution was carried out first with hexane and then with hexane:ethyl acetate (2:3) mixture to give 75% of the desired carbapenem as an oil.

IR (cm$^1$): 1780 (β-lactam C=O); 1743 (ester C=O) 1720 (olefin)

$^1$H NMR: δ:1.48 (CH$_3$; d; J= ~7.5 Hz); 3.44–3.5 (H6; dd; J=3 & 8.5 Hz); 4.26–4.4 (H5; ddd; J=3,9 & 10 Hz); 7.88 (s); 8.5 (s, Broad); 8.62 (s, Broad): pyridine H's

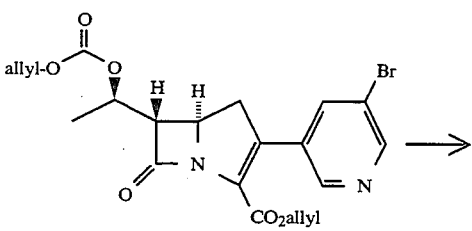

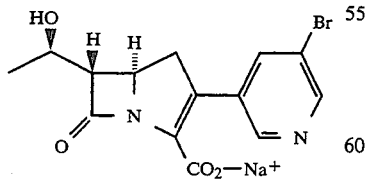

Step C: Preparation of Sodium (SR,6S)-2-[3-(5-bromo-pyridyl)]-6-[(1R)-hydroxyethyl]-carbapen-2-em-3-carboxylate To a stirred solution of the bis protected product of Example 1, Step B (93 mg; 0.2 mM) in 1:1 mixture of methylene chloride and ether (3 mL) in a centrifuge tube at 0° C. under nitrogen were added 2-ethylhexanoic acid (32 μl; 0.2 mM), triphenyl-phosphine (13 mg; 0.05 mM), Tetrakis-(triphenylphos-sphine)palladium (46 mg; 0.04 mM), and sodium 2-ethylhexanoate (33 mg; 0.2 mM) in that order. Within a few minutes, a precipitate separated. The reaction mixture was stirred vigorously at 0° C. for 2 hours, then diluted with 10 mL of ether and centrifuged. The supernatant liquid was separated and the solid was stirred with 2 mL of ethyl acetate, and centrifugation gave a solid, which was dissolved in 1 mL of water and applied on 1000 μ reverse phase silica gel plate. After eluting with acetonitrile:water (1:3) mixture, the U.V. active area was scraped and stirred in 4:1 mixture of acetonitrile and water (5 mL). After filtering, the solid was washed with 3×1 mL of the same solvent mixture. The filtrate was washed with 4×10 mL of hexane, concentrated in vacuo at R.T. to 1 ml and freeze dried to give 63% of the desired sodium salt as white fluffy solid.

UV(nm): λ$^{water}_{max}$=307 (68 $_{ext}$=7300)

$^1$H NMR: (D$_2$O) (δ): 1.22 (CH$_3$; d; J= ~7 Hz); 3.44–3.5 (H6; dd; J=3 & 6 Hz); 7.93, 8.35 & 8.44 (pyridine H's)

EXAMPLE 2

Sodium (5R,6S)-2-[3-(5-phenylpyridyl)]-6-[(1R)-hydroxyethyl]-carbapen-2-em-3-carboxylate

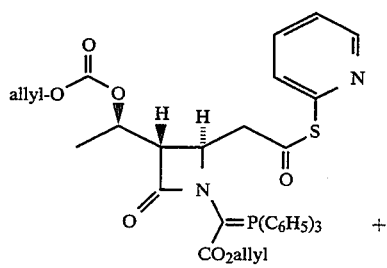

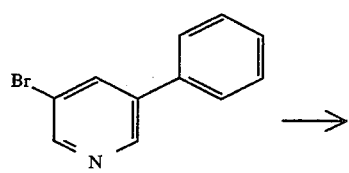

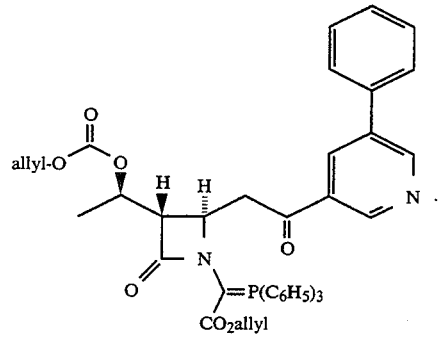

Step A: Preparation of (3S,4R)-1-[[(Allyloxy)carbony (triphenylphosphoranylidene)methyl]-3-[(1R) -1-[(allyloxycarbonyloxy)ethyl]-4-[(1R)-2'-[3-(5-phenyl-pyridyl)carbonyl]ethyl]azetidin-2-one

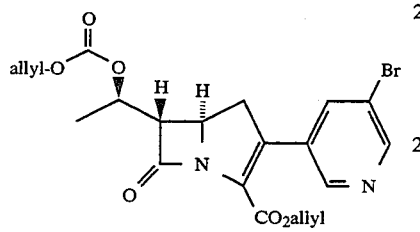

Following the procedure of Example 1, Step A and substituting 3-bromo-5-phenylpyridine for 3,5-dibromopyridine the title compound was obtained.

IR (cm$^{-1}$): 1740 ($\beta$-lactam C=O); 1685 (aromatic C=O); 1620 & 1645 (ylide).

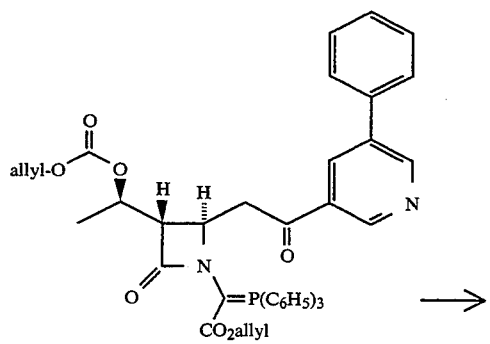

Step B: Preparation of Allyl (5R,6S)-2-[3-(5-phenyl)-pyridyl)]-6-[(1R)-allyloxycarbonyloxy-ethyl]-carbapen-2-em-3-carboxylate Following the procedure of Example 1, Step B the title compound was obtained, from the above product of Step A.

IR (cm$^{-1}$): 1780 ($\beta$-lactam C=O); 1740 (ester C=O);
$^1$H NMR $\delta$:1.5 (CH$_3$; d; J=~8 Hz); 3.44–3.52 (H6; dd; J=3 & 8 Hz); 4.3–4.44 (H5; ddd; J=3, 9&10 Hz); 7.95 (S), 8.59 (S, broad), 8.80 (S, broad)(pyridine H's); 7.4–7.62 (phenyl H's).

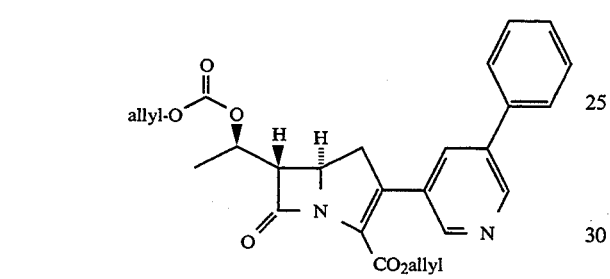

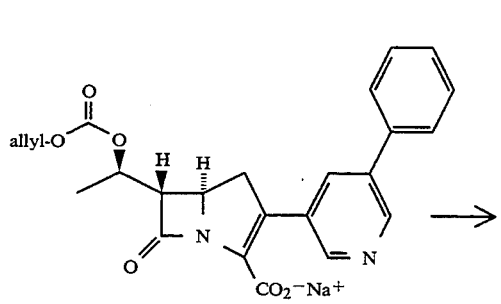

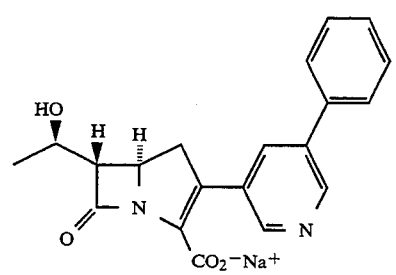

Step C: Preparation of Sodium (5R,6S)-2-[3-(5-phenyl -pyridyl)]-6-[(1R)-hydroxyethyl]-carbapen-2-em-3-carboxylate Following the procedure of Example 1, Step C the title compound was obtained, from the above product of step B.

UV: $\lambda^{H_2O}$ max=303 nm ($\epsilon_{ext}$=5723)

$^1$H NMR (D$_2$O) ($\delta$): 1.23 (CH$_3$; d; J=~8 Hz); 3.43–3.50 (H6); 7.9 (S), 8.33 (S, broad) & 8.53 (S, broad) (pyridine H's); 7.4–7.64 (phenyl H's).

EXAMPLE 3

Sodium (5R,6S)-2-[3-[5-(3-pyridyl)pyridyl]]-6-[(1R-hydroxyethyl]-carbapen-2-em-3-carboxylate

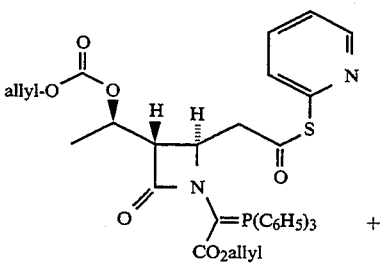
+

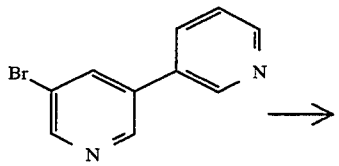

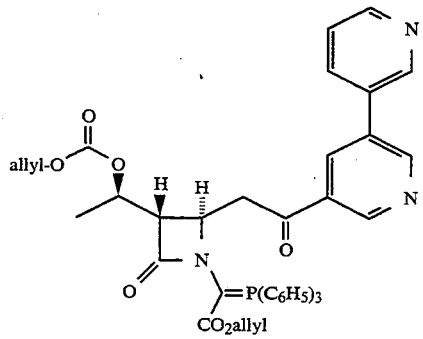

Step A: Preparation of (3S,4R)-1-[[(Allyloxy)carboxy-(triphenylphosphoranylidene)methyl]-3-[(1R) -1-[(allyloxycarbonyloxy)ethyl]-4-[(1R)-2'-[3-(5-(3-pyridyl)-pyridyl)carbonyl]ethyl]azetidin -2-one Following the procedure of Example 1, Step A and substituting 3-bromo-5-(3-pyridyl)pyridine for 3,5-dibromopyridine the title compound was obtained.

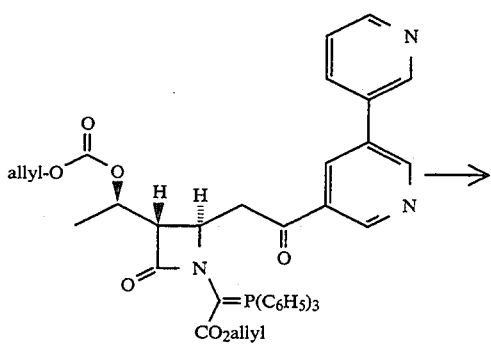

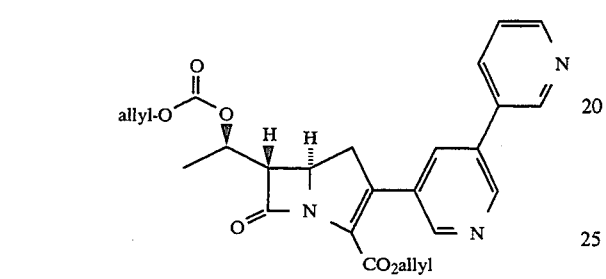

Step B: Preparation of Allyl (5R,6S)-2-[3-(5-(3-pyridyl)pyridyl)]-6-[(1R)-alloxycarbonyl-oxyethyl]-carbapen-2-em-3-carboxylate Following the procedure of Example 1, Step B the title compound was obtained, from the above product.

IR(cm$^{-1}$): 1780 ($\beta$-lactam C=O); 1740 (ester C=O)

$^1$H NMR ($\delta$): 1.5 (CH$_3$; d; J=~8 Hz); 3.44–3.52 (H6; dd; J=3 & 8 Hz); 4.3–4.43 (H5; ddd; J=3;9 & 10 Hz) 7.43; 7.9; 7.98; 8.62; 8.68; 8.78 & 8.85 (aromatic H's).

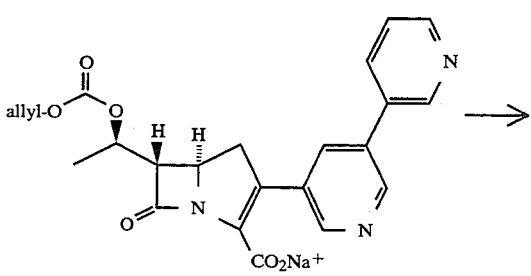

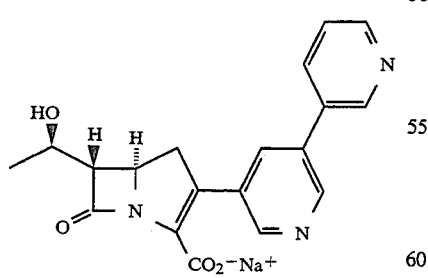

Step C: Preparation of Sodium (5R,6S)-2-[3-(5-<3-pyridyl)pyridyl)]-6-[(1R)-hydroxyethyl]carbapen-2-em-3-carboxylate Following the procedure of Example 1, Step C the title compound was obtained, from the above product.

UV: $\lambda^{water}_{max}$: 305 nm ($\delta_{ext}$=8472)

$^1$H NMR (D$_2$O) ($\delta$): 1.28 (CH$_3$; d; J=~8 Hz); 3.46–3.52 (H6; dd; J=3 & 6 Hz); 7.5; 7.94; 8.02; 8.45 (2 H's); 8.57; 8.67 (aromatic H's).

EXAMPLE 4

Sodium (5R,6S)-2-[3-(5-methylthiopyridyl)]-6-[(1R)-allyloxycarbonyloxyethyl]-carbapen-2-em-3-carboxylate

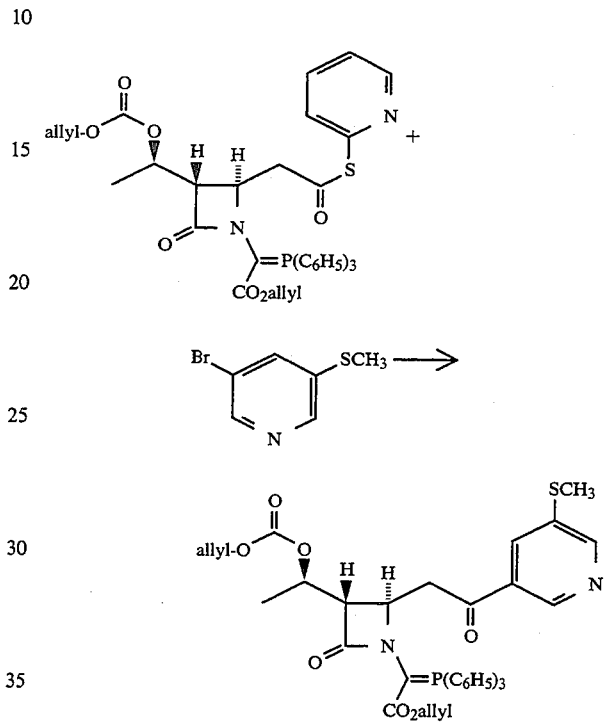

Step A: Preparation of (3S,4R)-1-[[(Allyloxy)-carbonyl(triphenylphosphoranylidene)methyl]-3-[(1R)-1-[(Allyloxycarbonyloxy)ethyl]-4-[(1R)-2'-[3-(5-methylthiopyridyl)carbonyl]-ethyl]azetidin-2-one Following the procedure of Example 1, Step A and substituting 3-bromo-5-thiomethylpyridine for 3,5-dibromopyridine the title compound was obtained.

IR (cm$^{-1}$): 1740 ($\beta$-lactam C=O); 1685 (aromatic C=O); 1620 & 1645 (ylide)

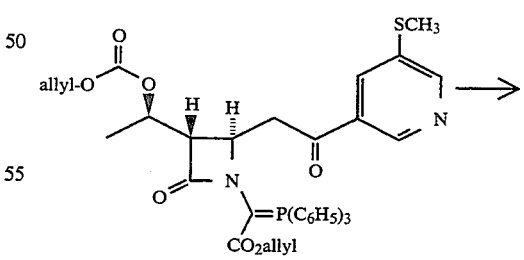

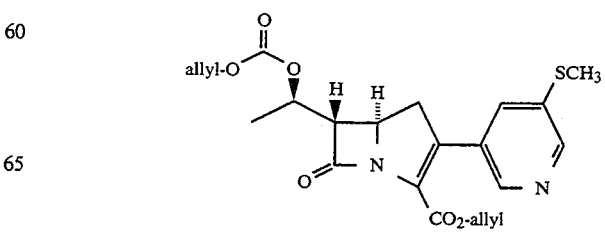

Step B: Preparation of Allyl (5R,6S)-2-[3-(5-methyl thiopyridyl]-6-[(1R)-allyloxycarbonyloxy -ethyl]-carbapen-2-em-3-carboxylate Following the procedure of Example 1, Step B the title compound was obtained, from the above product of Step A.

IR (cm$^{-1}$): 1785 ($\beta$-lactam C=O); 1740 (ester C=O)
$^1$H NMR ($\delta$): 1.49 (CH$_3$; d; J= ~8 Hz); 2.52 (SCH$_3$; s); 3.42–3.50 (H5; dd; J=3 & 8 Hz); 7.6 (H$_4$ of pyridine; dd, J=1.5 & 2 Hz); 8.32 & 8.44 (H2 & H6 of pyridine)

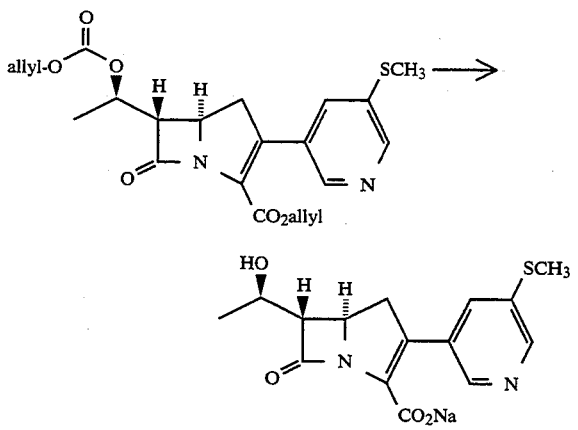

Step C: Preparation of Sodium (5R,6S)-2-[3-(5-methyl -thio)pyridyl]-6-[(1R)-allyloxycarbonyloxy -ethyl]-carbapen-2-em-3-carboxylate Following the procedure of Example 1, Step C the title compound was obtained, from the above product of Step B.

UV: $\lambda^{water}_{max}$305 nm ($\epsilon_{ext}$=6156)
$^1$H NMR (D$_2$O) ($\delta$): 1.27 (CH$_3$; d; J= ~8 Hz); 3.46–3.52 (H5; dd; J=3 & 6 Hz); 7.68 (H$_4$ of pyridine); 8.26 (H2 & H6 of pyridine; broad)

EXAMPLE 5

Sodium (5R, 6S)-2-[3-(5-methylsulfonylpyridyl)]-6-[(1R)hydroxyethyl]-carbapen-2-em-3-carboxylate

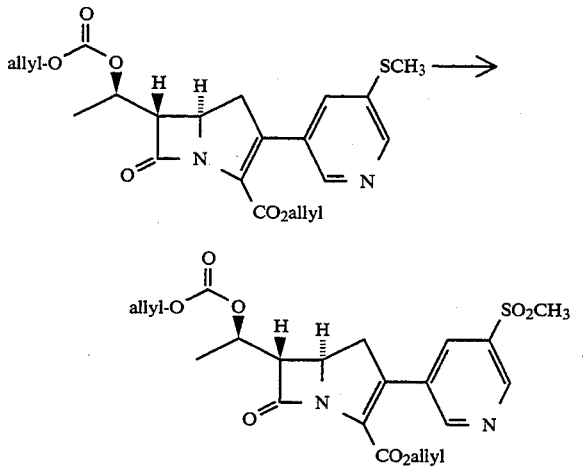

Step A: Preparation of Allyl (5R,6S)-2-[B-(5-methyl -sulfonylpyridyl)]-6-[(1R)-allyloxycarbonyl -oxyethyl]-carbapen-2-em-3carboxylate To a vigorously stirred solution pyridyl-carbapenem (R$^3$=SCH$_3$) (78 mg; 0.2 mM) were added 1.6 mL of 0.5M solution of sodium bicarbonate followed by 86 mg (0.5 mM) of m-chloroperbenzoic acid. This reaction mixture was stirred 1 hour at R.T. 5 mL of 5% solution of sodium thiosulfate was added, and stirring was continued for 1 hour. After diluting with 10 mL of ethyl acetate, the reaction mixture was washed with 3×5 mL of saturated sodium chloride solution, dried over anhydrous magnesium sulfate. Solvent removal gave a crude oil, which was chromatographed on silica gel using hexane:ethyl acetate (2:1) mixture to give 32 mg of the desired carbapenem-sulfone as an oil.

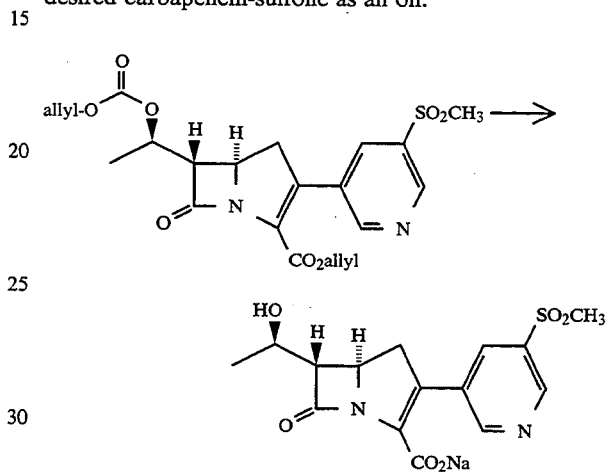

Step B: Preparation of Sodium (5R,6S)-2-[3-(5-methyl -sulfonylpyridyl)]-6-[(1R)-hydroxyethyl]-carbapen-2-em-3-carboxylate Following the procedure of Example 1, Step C the title compound was obtained, from the above product of Step A.

UV: $\lambda^{water}_{max}$: 310 nm ($\epsilon_{ext}$=8527)
$^1$H NMR (D$_2$O) ($\delta$): 1.67 (CH$_3$; d; J= ~8 Hz); 3.67 (SCH$_3$; S); 8.67 (H$_4$ of pyridine); 9.13 & 9.27 (H2 & H6 of pyridine)

EXAMPLE 6

Sodium (5R,6S)-2-[3-(5-methylsulfinylpyridyl)]-6-[(1R)-hydroxyethyl]-carbapen-2-em-3-carboxylate

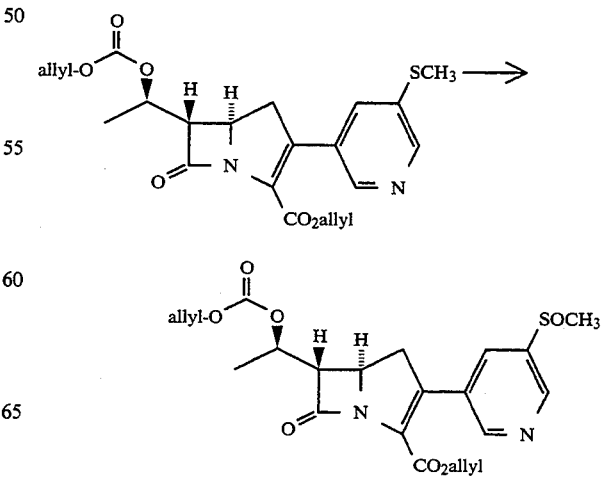

Step A: Preparation of Allyl (5R,6S)-2-[3-(5-methyl-sulfinylpyridyl)]-6-[(1R)-allyloxycarbonyl-oxyethyl]-carbapen-2-em-3-carboxylate Following the procedure of Example 5, Step A with the exception that one equivalent of m-chloroperbenzoic acid is used, the title compound is obtained.

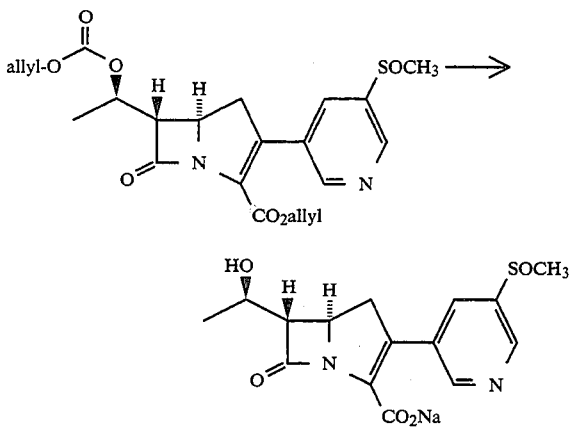

Step B: Preparation of Sodium (5R,6S)-2-[3-(5-methyl-sulfinylpyridyl)]-6-[(1R)-hydroxyethyl]-carbapen-2-em-3-carboxylate Following the procedure of Example 1, Step C and substituting the product of Example 6, Step A the title compound is obtained.

EXAMPLE 7

(5R,6S)-2-[3-(5-methylthio-1-methylpyridyl)]-6-[(1R)-hydroxyethyl]-carbapen-2em-3-carboxylate

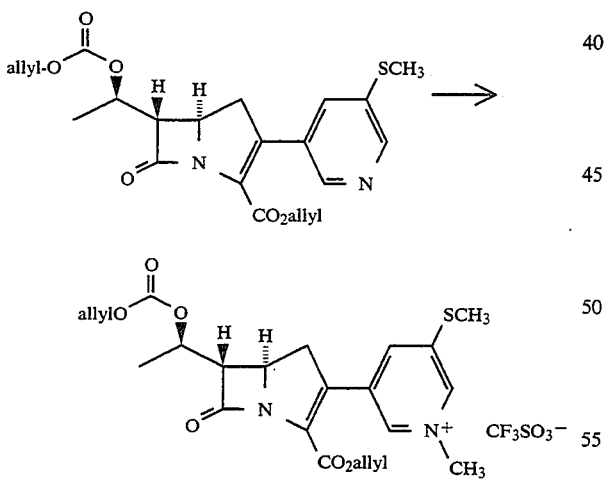

Step A: Preparation of Allyl, [trifluoromethane-sulfonyl (5R,6S)-2-[3-(5-methylthio-1-methylpyridinium)]]-6-[(1R)-allyloxycarbonyl-oxyethyl]carbapen-2-em-3-carboxylate Methyl trifluoromethanesulfonate (34 μL; 0.3 mM) was added to a solution of the product of Example 4, Step B (110 mg; 0.25 mM) in 3 mL of methylene chloride under nitrogen at 0° C. After 1 hour stirring, solvent and excess methylating agent were removed in vacuo at room temperature.

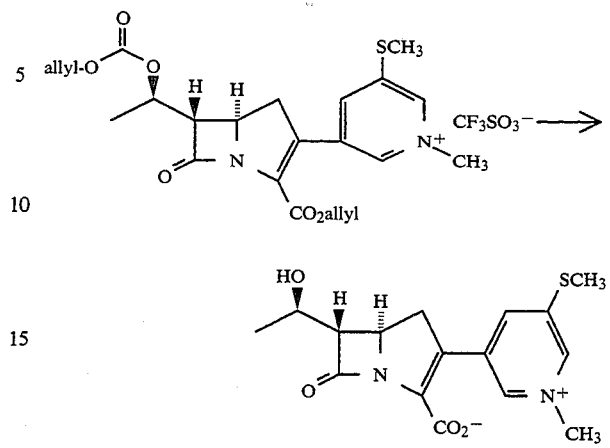

Step B: Preparation of (5R,6S)-2-[3-(5-methyl-thio-1-methylpyridinium)]-6-[(1R)-hydroxy-ethyl]-carbapen-2-em-3-carboxylate Following the procedure of Example 1, Step C and substituting the product of Example 7, Step A the title compound was obtained as a yellow solid in 12%.

UV: $\lambda^{water}_{max} = \sim 330$ nm ($\epsilon_{ext} = 2138$)

$^1$H NMR (D$_2$O) (δ): 1.58 (CH$_3$; d; J= ~8 Hz); 2.88 (SCH$_3$; s); 4.57 (NCH$_3$; s); 8.48 (s); 8.7 (s); 8.74 (s) (pyridine H's)

EXAMPLE 8

(5R,6S)-2-[3-(5-bromo-1-methylpyridyl)]-6-[(1R)-hydroxyethyl]-carbapen-2-em-3-carboxylate

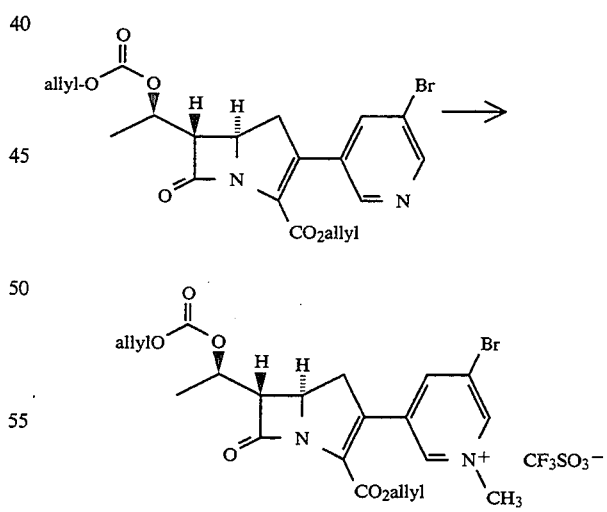

Step A: Preparation of Allyl, [trifluoromethane-sulfonyl (5R,6S)-2-[3-(5-bromo-1-methyl-pyridinium)]]-6-[(1R)-allyloxycarbonyloxy-ethyl]-carbapen-2-em-3-carboxylate Following the procedure of Example 7, Step A and substituting the product of Example 1, Step B the title compound is obtained.

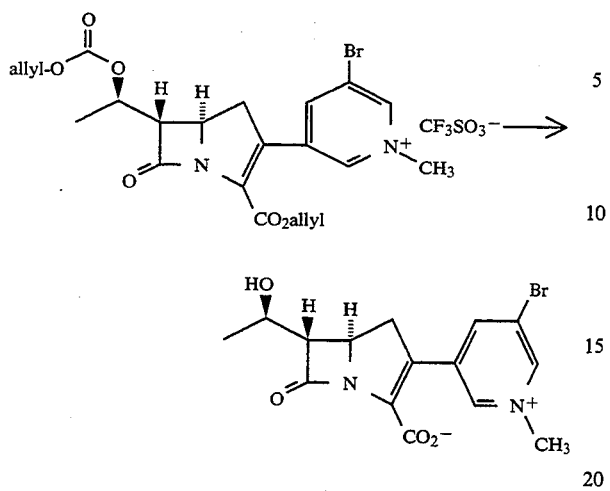

Step B: Preparation of (5R,6S)-2-[3-(5-bromo -1-methylpyridinium)]-6-[(1R)-hydroxy -ethyl]-carbapen-2-em-3-carboxylate Following the procedure of Example 7, Step B and substituting the product of Example 8, Step A the title compound is obtained.

EXAMPLE 9

(5R,6S)-2-[3-(5-phenyl-1-methylpyridyl)]-6-[(1R)-hydroxyethyl]-carbapen-2-em-3-carboxylate

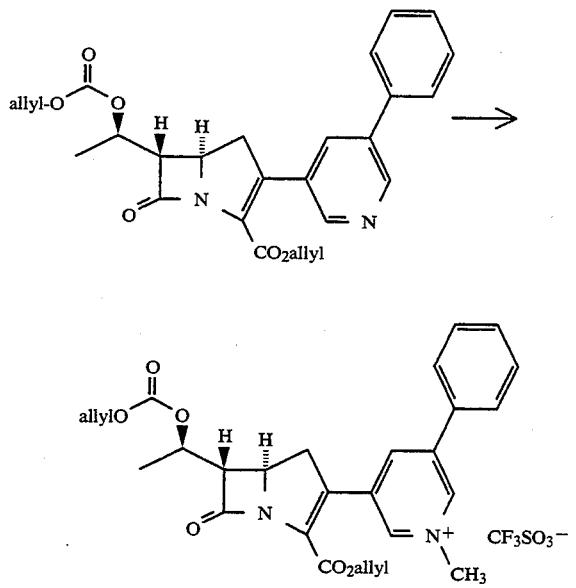

Step A: Preparation of Allyl, [trifluoromethane -sulfonyl (5R,6S)-2-[3-(5-phenyl-1-methyl -pyridinium)]]-6-[(1R)-allyloxycarbonyloxy -ethyl]-carbapen-2-em-3-carboxylate Following the procedure of Example 7, Step A and substituting the product of Example 2, Step B the title compound is obtained.

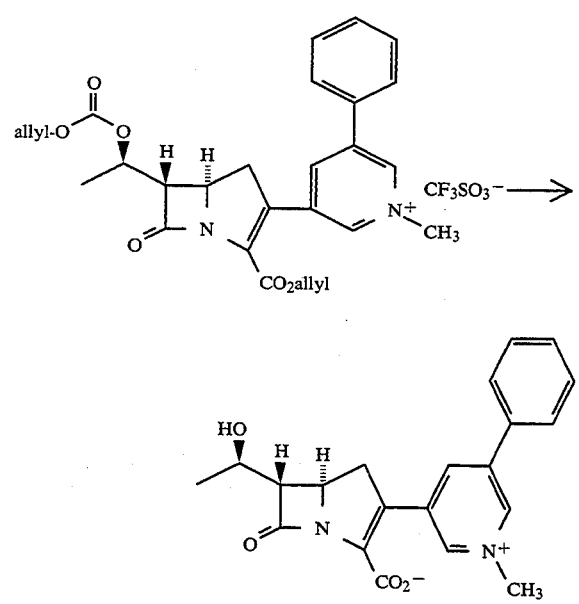

Step B: Preparation of (5R,6S)-2-[3-(5-phenyl -1-methylpyridinium)]-6-[(1R)-hydroxy -ethyl]-carbapen-2-em-3-carboxylate Following the procedure of Example 7, Step B and substituting the product of Example 9, Step A the title compound is obtained.

Preparation of Intermediate Synthons
3-Bromo-5-phenylpyridine

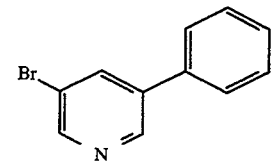

Tetrakis(triphenylphosphine)palladium (577 mg; 0.5 mM) was added to 3,5-dibromopyridine (5.214 g; 22 mM) in 40 mL of toluene at R.T. under nitrogen. After 10 minutes stirring, 25 mL of 2M aqueous sodium carbonate solution, phenylboronic acid (2.44 g; 20 mM), and 10 mL of ethanol were added, and the mixture was heated 11 hours at 80° C. The reaction mixture was cooled, diluted with 75 mL of ethyl acetate and washed with 2×15 mL of saturated sodium carbonate solution, and then dried over anhydrous magnesium sulfate. Solvent removal gave crude product, which was chromatographed on silica gel using ethyl acetate:hexane (1:5) mixture to give a white solid boiling at 100°–101° C./~0.1 mm in 28% yield.

3-Bromo-5-(3-pyridyl)pyridine

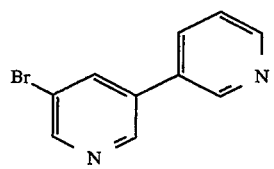

Tetrakis(triphenylphosphine)palladium (915 mg; 0.75 mM) was added to a solution of 3,5-dibromopyridine (4.74 g, 20 mM) in 75 mL of tetrahydrofuran. After stirring for 5 minutes tetra-n-butylammonium bromide (483 mg; 1.5 mM), finely powdered potassium hydroxide (2.52 g; 45 mM) and 3-pyridyldiethylborane (2.2 g; 15 mM) were added and the resulting reaction mixture was heated to reflux for 2 hours. The reaction mixture was cooled, diluted with 100 mL of ethyl acetate and washed with 10×25 mL of saturated sodium chloride solution and dried over anhydrous magnesium sulfate. Solvent removal gave the crude product which was chromatographed on silica gel using ethyl acetate to give the desired product as a solid, boiling at 135°-6° C./~1 mm in 33% yield.

3-Bromo-5-methylthiopyridine

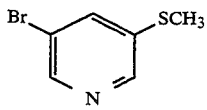

3,5-dibromopyridine (4.74 g; 20 mM) was added to 80 mL of ether at −78° C. under nitrogen. After 5 mins. of vigorous stirring, n-butyllithium [8.4 mL (2.5M); 21 mM] was added dropwise, and the reaction mixture was stirred at −78° C. for 0.5 hour Methyl disulfide (3.6 mL; 40 mM) was then added dropwise and the mixture was stirred overnight as it warmed to R.T. 20 mL of saturated ammonium chloride was slowly added. After diluting with 100 mL of ethyl acetate, the reaction mixture was washed with 2×20 mL of saturated sodium chloride solution, and Solvent was dried over anhydrous magnesium sulfate. removed to give oily product, which was chromatographed on silica gel using ether:-hexane (1:4) mixture to give 2.3 g of the product. This product distilled at 107°-8° C./~1 mm to yield 49% of the desired methylthioether.

$^1$H-NMR (δ): 2.52 (SCH$_3$; S); 7.68 (H4; dd=1.5 & 2.5 Hz); 8.38–8.44 (H1 & H6)

What is claimed is:

1. A compound of formula I

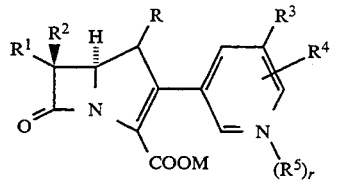

R is H or CH$_3$;

R$^1$ and R$^2$ are independently H, CH$_3$—, CH$_3$CH$_2$—, (CH$_3$)$_2$CH—, HOCH$_2$—, CH$_3$CH(OH)—, (CH$_3$)$_2$C(OH)—, FCH$_2$CH(OH)—, F$_2$CHCH(OH)—, F$_3$CCH(OH)—, CH$_3$CH(F)—, CH$_3$CF$_2$—, or (CH$_3$)$_2$C(F)—;

R$^3$ is a) a halogen atom selected from the group consisting of —Br, —Cl, —F, and —I;

b) a sulfur radical which is —S(O)$_n$R$^s$, where n=0–2, and R$^s$ is as defined below;

c) aryl, where aryl is phenyl or napthyl optionally mono-substituted with R$^4$ as defined below; or d) heteroaryl, where heteroaryl is a monocyclic aromatic hydrocarbon group having 5 or 6 ring atoms, in which a carbon atom is the point of attachment, in which one of the carbon atoms has been replaced by a nitrogen atom, in which one additional carbon atom is optionally replaced by a heteroatom selected from O or S, in the case of a 5-membered heterocycle, and in which from 1 to 3 additional carbon atoms are optionally replaced by a nitrogen heteroatom, and where the heteroaryl is optionally mono-substituted with R$^4$, as defined below; and R$^4$ is hydrogen or is selected from the group consisting of:

a) a trifluoromethyl group which is —CF$_3$;

b) C$_1$-C$_4$ alkoxy radical: —OC$_{1-4}$ alkyl, wherein the alkyl is optionally monosubstituted by R$^q$, where R$^q$ is a member selected from the group consisting of —OH, —OCH$_3$, —CN, —C(O)NH$_2$, —OC(O)NH$_2$, CHO, —OC(O)N(CH$_3$)$_2$, —SO$_2$NH$_2$, —SO$_2$N(CH$_3$)$_2$, —SOCH$_3$, —SO$_2$CH$_3$, —F, —CF$_3$, —COOM$^a$ (where M$^a$ selected from the group consisting of is hydrogen, alkali metal, methyl and phenyl), tetrazolyl (where the point of attachment is the carbon atom of the tetrazole ring and one of the nitrogen atoms is mono-substituted by M$^a$ as defined above) and —SO$_3$M$^b$ (where M$^b$ is hydrogen or an alkali metal);

c) a hydroxy group which is —OH;

d) a carbonyloxy radical which is —O(C=O)R$^s$, where

R$^s$ is C$_{1-4}$ alkyl or phenyl, each of which is optionally mono-substituted by R$^q$ as defined above;

e) a carbamoyloxy radical which is —O(C=O)N-(R$^y$)R$^z$, where

R$^y$ and R$^z$ are independently H, C$_{1-4}$ alkyl (optionally mono-substituted by R$^q$ as defined above), together a 3- to 5-membered alkylidene radical to form a ring (optionally substituted with R$^q$ as defined above) or together a 2- to 4-membered alkylidene radical, interrupted by —O—, —S—, —S(O)— or —S(O)$_2$— to form a ring (where the ring is optionally mono-substituted with R$^q$ as defined above);

f) a sulfur radical which is —S(O)$_n$—R$^s$ where n=0–2, and R$^s$ is defined above;

g) a sulfamoyl group which is —SO$_2$N(R$^y$)R$^z$ where R$^y$ and R$^z$ are as defined above;

h) azido which is N$_3$;

i) a formamido group which is —N(R$^t$)(C=O)H, where

R$^t$ is H or C$_{1-4}$ alkyl, and the alkyl thereof is optionally monosubstituted by R$^q$ as defined above;

j) a (C$_1$-C$_4$ alkyl)carbonylamino radical which is —N(R$^t$)(C=O)C$_{1-4}$ alkyl, where R$^t$ is as defined above, and the alkyl group is also optionally mono-substituted by R$^q$ as defined above;

k) a (C$_1$-C$_4$ alkoxy)carbonylamino radical which is —N(R$^t$)(C=O)OC$_{1-4}$ alkyl, where R$^t$ is as defined above, and the alkyl group is also optionally mono-substituted by R$^q$ as defined above;

l) a ureido group which is —N(R$^t$)(C=O)N(R$^y$)R$^z$ where R$^t$, R$^y$ and R$^z$ are as defined above;

m) a sulfonamido group which is —N(R$^t$)SO$_2$R$^s$, where R$^s$ and R$^t$ are as defined above;

n) a cyano group which is —CN;

o) a formyl or acetalized formyl radical which is —(C=O)H or —CH(OCH$_3$)$_2$;

p) (C$_1$-C$_4$ alkyl)carbonyl radical wherein the carbonyl is acetalized: —C(OCH$_3$)$_2$C$_{1-4}$ alkyl, where the alkyl is optionally mono-substituted by R$^q$ as defined above;

q) carbonyl radical which is —(C=O)R$^s$, where R$^s$ is as defined above;

r) —(C=NOR$^z$)R$^y$ where R$^y$ and R$^z$ are as defined above, except they may not be joined together to form a ring;

s) a (C$_1$-C$_4$ alkoxy)carbonyl radical which is —(C=O)OC$_{1-4}$ alkyl, where the alkyl is optionally mono-substituted by R$^q$ as defined above;

t) a carbamoyl radical which is —(C=O)N(R$^y$)R$^z$ where R$^y$ and R$^z$ are as defined above;

u) an N-hydroxycarbamoyl or N(C$_1$-C$_4$ alkoxy)carbamoyl radical in which the nitrogen atom may be additionally substituted by a C$_1$-C$_4$ alkyl group which is —(C=O)—N(OR$^y$)R$^z$ where R$^y$ and R$^z$ are as defined above, except they may not be joined together to form a ring;

v) a thiocarbamoyl group which is —(C=S)N(R$^y$)R$^z$ where R$^y$ and R$^z$ are as defined above;

w) carboxyl which is —COOM$^b$, where M$^b$ is as defined above;

x) thiocyanate which is —SCN;

y) trifluoromethylthio which is —SCF$_3$;

z) an amino group, N(R$^t$)$_2$, wherein R$^t$ is as defined above;

aa) an anionic function selected from the group consisting of:
phosphono: [P=O(OM$^b$)$_2$]; alkylphosphono: {P=O(CM$^b$)—[O(C$_1$-C$_4$ alkyl)]}; alkylphosphinyl: [P=)(OM$^b$)—(C$_1$-C$_4$-alkyl)]; phosphoramido: [P=O(OM$^b$)N(R$^y$)R$^z$ and P=O(OM$^b$)NHR$^x$]; sulfino: (SO$_2$M$^b$); sulfo: (SO$_3$M$^b$); acylsulfonamides selected from the structures: CONM$^b$SO$_2$R$^x$, CONM$^b$SO$_2$N(R$^y$)R$^z$, SO$_2$NM$^b$CON(R$^y$)R$^z$; and SO$_2$NM$^b$CN, where R$^x$ is phenyl or heteroaryl, where heteroaryl is a monocyclic aromatic hydrocarbon group having 5 or 6 ring atoms, in which a carbon atom is the point of attachment, in which one of the carbon atoms has been replaced by a nitrogen atom, in which one additional carbon atom is optionally replaced by a heteroatom selected from O or S, and in which from 1 to 2 additional carbon atoms are optionally replaced by a nitrogen heteroatom, and where the phenyl and heteroaryl are optionally monosubstituted by R$^q$, as defined above; M$^b$ is as defined above; and R$^y$ and R$^z$ are as defined above;

ab) C$_5$-C$_7$ cycloalkyl group in which one of the carbon atoms in the ring is replaced by a heteroatom selected from O, S, NH, or N(C$_1$-C$_4$ alkyl) and in which one additional carbon may be replaced by NH or N(C$_1$-C$_4$ alkyl), and in which at least one carbon atom adjacent to each nitrogen heteroatom has both of its attached hydrogen atoms replaced by one oxygen thus forming a carbonyl moiety and there are one or two carbonyl moieties present in the ring;

ac) C$_2$-C$_4$ alkenyl radical, optionally mono-substituted by one of the substituents a) to ac) above and phenyl which is optionally substituted by R$^q$ as defined above;

ad) C$_2$-C$_4$ alkynyl radical, optionally mono-substituted by one of the substituents a) to ac) above;

ae) C$_1$-C$_4$ alkyl radical;

af) C$_1$-C$_4$ alkyl mono-substituted by one of the substituents a)-ac) above;

ag) a 2-oxazolidinonyl moiety in which the point of attachment is the nitrogen atom of the oxazolidinone ring, the ring oxygen atom is optionally replaced by a heteroatom selected from S and NR$^t$ (where R$^t$ is as defined above) and one of the saturated carbon atoms of the oxazolidinone ring is optionally mono-substituted by one of the substituents a) to ag) above;

ah) aryl, where aryl is phenyl or napthyl optionally mono-substituted with R$^q$ ai) heteroaryl, where heteraryl is a monocyclic aromatic hydrocarbon group having 5 ring atoms, in which a carbon atom is the point of attachment, in which one of the carbon atoms has been replaced by a heteroatom selected from O or S;

R$^5$ is amino (NH$_2$), oxygen or (C$_1$-C$_4$)alkyl; and r is 0 or 1; and

M is selected from the group consisting of
 i) hydrogen;
 ii) a pharmaceutically acceptable esterifying group or removable carboxyl protecting group;
 iii) an alkali metal or other pharmaceutically acceptable cation; and
 iv) a negative charge when r is 1 which is balanced by a cation or a pharmaceutically acceptable salt thereof.

2. The compound of claim 1, wherein R$^1$ is hydrogen and R$^2$ is (R)—CH$_3$CH(OH)— or (R)—CH$_3$CH(F).

3. The compound of claim 2 wherein R$^3$ is selected from the group consisting of: F, Cl, Br, I, SMe, SO$_2$Me, phenyl and 3-pyridyl.

4. The compound of claim 3 wherein R$^4$ is selected from the group consisting of:

| | |
|---|---|
| —OCH$_3$ | —NH$_2$ |
| —OCH$_2$CH$_2$OH | —OCH$_2$CO$_2$Na |
| —F | —CF$_3$ |
| —Br | —Cl |
| —OH | —I |
| —OCONH$_2$ | —OCOCH$_3$ |
| —SOCH$_3$ | —SCH$_3$ |
| —SCH$_2$CH$_2$OH | —SO$_2$CH$_3$ |
| —SO$_2$NH$_2$ | —SOCH$_2$CH$_2$OH |
| —NHCHO | —SO$_2$N(CH$_3$)$_2$ |
| —NHCO$_2$CH$_3$ | —NHCOCH$_3$ |
| —CN | —NHSO$_2$CH$_3$ |
| —COCH$_3$ | —CHO |
| —CH=NOH | —COCH$_2$OH |
| —CH=NOCH$_2$CO$_2$H | —CH=NOCH$_3$ |
| —SO$_2$CH$_2$CH$_2$OH | —CH=NOCMe$_2$CO$_2$H |
| —CH=NOCMe$_2$CO$_2$Me | —CO$_2$CH$_2$CH$_2$OH |
| —CONH$_2$ | —CONHCH$_3$ |
| —CON(CH$_3$)$_2$ | —CONHCH$_2$CN |
| —CONHCH$_2$CONH$_2$ | —CONHCH$_2$CO$_2$H |
| —CONHOH | —CONHCH$_3$ |
| -tetrazolyl | —CO$_2$Na |
| —SCF$_3$ | —PO$_3$NaH |
| —CONHSO$_2$Ph | —CONHSO$_2$NH$_2$ |
| —SO$_3$Na | —SO$_2$NHCN |
| —SO$_2$NHCONH$_2$ | —CH=CHCN |
| —CH=CHCONH$_2$ | —CH=CHCO$_2$Na |
| —C≡C—CONH$_2$ | —C≡C—CN |
| —CH$_2$OH | —CH$_2$N$_3$ |
| —CH$_2$CO$_2$Na and | —CH$_2$I. |

5. A compound wherein the structural formula is:

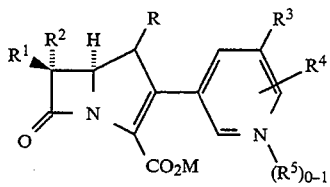

and the substituents are as defined in the Table I below and when $R^5$ is present the pyridyl nitrogen carries a positive charge which in turn is counterbalanced by M being negatively charged:

TABLE I

| Ex. | R | $R^2$ | M | $R^3$ | $R^4$ | $R^5$ |
|---|---|---|---|---|---|---|
| 1 | H | CH(OH)CH$_3$ | Na$^+$ | Br | H | — |
| 2 | H | CH(OH)CH$_3$ | Na$^+$ | phenyl | H | — |
| 3 | H | CH(OH)CH$_3$ | Na$^+$ | 3-pyridyl | H | — |
| 4 | H | CH(OH)CH$_3$ | Na$^+$ | SCH$_3$ | H | — |
| 5 | H | CH(OH)CH$_3$ | Na$^+$ | SO$_2$CH$_3$ | H | — |
| 6 | H | CH(OH)CH$_3$ | Na$^+$ | SOCH$_3$ | H | — |
| 7 | H | CH(OH)CH$_3$ | (−) | SCH$_3$ | H | CH$_3$ |
| 8 | H | CH(OH)CH$_3$ | (−) | Br | H | CH$_3$ |
| 9 | H | CH(OH)CH$_3$ | (−) | phenyl | H | CH$_3$ |
| 10 | H | CH(OH)CH$_3$ | (−) | SOCH$_3$ | H | CH$_3$ |
| 11 | H | CH(OH)CH$_3$ | (−) | SO$_2$CH$_3$ | H | CH$_3$ |
| 12 | H | CH(F)CH$_3$ | Na$^+$ | Br | H | — |
| 13 | H | CH(F)CH$_3$ | (−) | Br | H | CH$_3$ |
| 14 | H | CH(F)CH$_3$ | Na$^+$ | phenyl | H | — |
| 15 | H | CH(F)CH$_3$ | (−) | phenyl | H | CH$_3$ |
| 16 | H | CH(F)CH$_3$ | Na$^+$ | 3-pyridyl | H | — |
| 17 | H | CH(F)CH$_3$ | Na$^+$ | SCH$_3$ | H | — |
| 18 | H | CH(F)CH$_3$ | Na$^+$ | SOCH$_3$ | H | — |
| 19 | H | CH(F)CH$_3$ | Na$^+$ | SO$_2$CH$_3$ | H | — |
| 20 | H | CH(F)CH$_3$ | (−) | SCH$_3$ | H | CH$_3$ |
| 21 | H | CH(F)CH$_3$ | (−) | SOCH$_3$ | H | CH$_3$ |
| 22 | H | CH(F)CH$_3$ | (−) | SO$_2$CH$_3$ | H | CH$_3$ |
| 23 | CH$_3$ | CH(OH)CH$_3$ | Na$^+$ | Br | H | — |
| 24 | CH$_3$ | CH(OH)CH$_3$ | Na$^+$ | SCH$_3$ | H | — |
| 25 | CH$_3$ | CH(F)CH$_3$ | Na$^+$ | Br | H | — |
| 26 | CH$_3$ | CH(F)CH$_3$ | Na$^+$ | SCH$_3$ | H | — |
| 27 | H | CH(OH)CH$_3$ | H | Br | NH$_2$ | — |
| 28 | H | CH(OH)CH$_3$ | (−) | Br | NH$_2$ | CH$_3$ |
| 29 | H | CH(OH)CH$_3$ | Na$^+$ | Br | CHO | — |
| 30 | H | CH(OH)CH$_3$ | Na$^+$ | SCH$_3$ | CHO | — |
| 31 | H | CH(OH)CH$_3$ | H | SCH$_3$ | NH$_2$ | — |
| 32 | H | CH(OH)CH$_3$ | (−) | SCH$_3$ | NH$_2$ | CH$_3$ |

6. A compound selected from the group consisting of:
Sodium (5R, 6S)-2-[3-(5-bromopyridyl)-6-[(1R)-hydroxyethyl]-carbapen-2-em-3-carboxylate;
Sodium (5R, 6S)-2-[3-(5-phenylpyridyl) ]-6-[(1R)-hydroxyethyl ]-carbapen-2-em-3-carboxylate;
Sodium (5R,6S)-2-[3-[5-(3-pyridyl)pyridyl]]-6-[(1R)-hydroxyethyl]-carbapen-2-em-3-carboxylate;
Sodium (5R,6S)-2-[3-(5-thiomethylpyridyl)]-6-[(1R)-allyloxycarbonyloxyethyl ]-carbapen-2-em-3-carboxylate;
Sodium (5R,6S)-2-[3-(5-methylsulfonylpyridyl)]-6-[(1R)-hydroxyethyl]-carbapen-2-em-3-carboxylate; and
(5R,6S)-2-[3-(5-thiomethyl-1-methylpyridyl)]-6-[(1R)-hydroxyethyl]-carbapen-2-em-3-carboxylate.

7. A pharmaceutical composition for antibacterial use comprising an antibacterially effective amount of a compound of claim 1 and a pharmaceutically acceptable carrier.

8. A pharmaceutical composition for antibacterial use comprising an antibacterially effective amount of a compound of claim 1, an inhibitorily effective amount of a dehydropeptidase (DHP) inhibitor, and optionally, a pharmaceutically acceptable carrier.

9. The pharmaceutical composition according to claim 8, wherein the DHP inhibitor is 7-(L-2-amino-2-carboxyethylthio)-2-(2,2-dimethyl-cyclopropanecarboxamide) -2-heptenoic acid.

10. The method according to claim 9, wherein the DHP inhibitor is 7-(L-2-amino-2-carboxyethyl thio)-2-(2,2-dimethylcyclopropane-carboxamide) -2-heptenoic acid.

11. A method of treating a bacterial infection in a mammalian patient in need of such treatment, comprising administering to such patient a compound in accordance with claim 1 in an amount effective to treat said bacterial infection.

12. A method of treating a bacterial infection in a mammalian patient in need of such treatment in accordance with claim 11, further comprising administering to such patient an inhibitorily effective amount of a DHP inhibitor.

* * * * *